(12) United States Patent
Le Comte et al.

(10) Patent No.: US 7,963,152 B2
(45) Date of Patent: Jun. 21, 2011

(54) MODULAR DEVICE FOR ANALYZING A BIOLOGICAL FLUID, SUCH AS BLOOD

(75) Inventors: Roger Le Comte, Perols (FR); Guilhem Couderc, Saint Jean de Vedas (FR); Didier Cremien, Sussargues (FR); Paul Moreno, Montpellier (FR)

(73) Assignee: Horiba ABX SAS (FR)

( * ) Notice: Subject to any disclaimer, the term of this patent is extended or adjusted under 35 U.S.C. 154(b) by 527 days.

(21) Appl. No.: 12/088,904

(22) PCT Filed: Sep. 19, 2006

(86) PCT No.: PCT/FR2006/050904
§ 371 (c)(1),
(2), (4) Date: Apr. 12, 2008

(87) PCT Pub. No.: WO2007/042691
PCT Pub. Date: Apr. 19, 2007

(65) Prior Publication Data
US 2008/0250849 A1   Oct. 16, 2008

(30) Foreign Application Priority Data
Oct. 7, 2005   (FR) ..................................... 05 10286

(51) Int. Cl.
*G01N 1/00* (2006.01)
(52) U.S. Cl. .................................................... 73/64.56
(58) Field of Classification Search ................... 73/64.56
See application file for complete search history.

(56) References Cited

U.S. PATENT DOCUMENTS

| | | | |
|---|---|---|---|
| 5,595,712 A | 1/1997 | Harbster et al. | |
| 5,788,927 A | 8/1998 | Farrell et al. | |
| 6,453,257 B1 * | 9/2002 | Juhasz | 702/114 |
| 6,536,477 B1 | 3/2003 | O'Connor et al. | |
| 6,619,112 B2 * | 9/2003 | Juhasz | 73/168 |
| 2005/0082351 A1 | 4/2005 | Pinchot | |
| 2006/0065046 A1 * | 3/2006 | Battiston et al. | 73/61.79 |

FOREIGN PATENT DOCUMENTS

| | | |
|---|---|---|
| EP | 1 203 954 A2 | 5/2002 |
| FR | 2 841 653 A1 | 1/2004 |
| FR | 2 862 387 | 5/2005 |

* cited by examiner

*Primary Examiner* — Hezron Williams
*Assistant Examiner* — Rodney T Frank
(74) *Attorney, Agent, or Firm* — Fitch, Even, Tabin & Flannery

(57) ABSTRACT

The invention relates to a modular device for implementation in a biological fluid analysis system. It comprises functional modules, each comprising a support for supporting hydraulic components, the support including at least two plates having etched therein circuits that enable channels to be defined when the two plates are assembled side by side. According to the invention, said functional modules comprise at least a preparation first functional module for preparing a fluid for analysis and supporting at least one dilution vessel, and an injection second functional module for injecting the fluid prepared in said dilution vessel towards an analysis unit, said first and second modules being connected to one another.

15 Claims, 5 Drawing Sheets

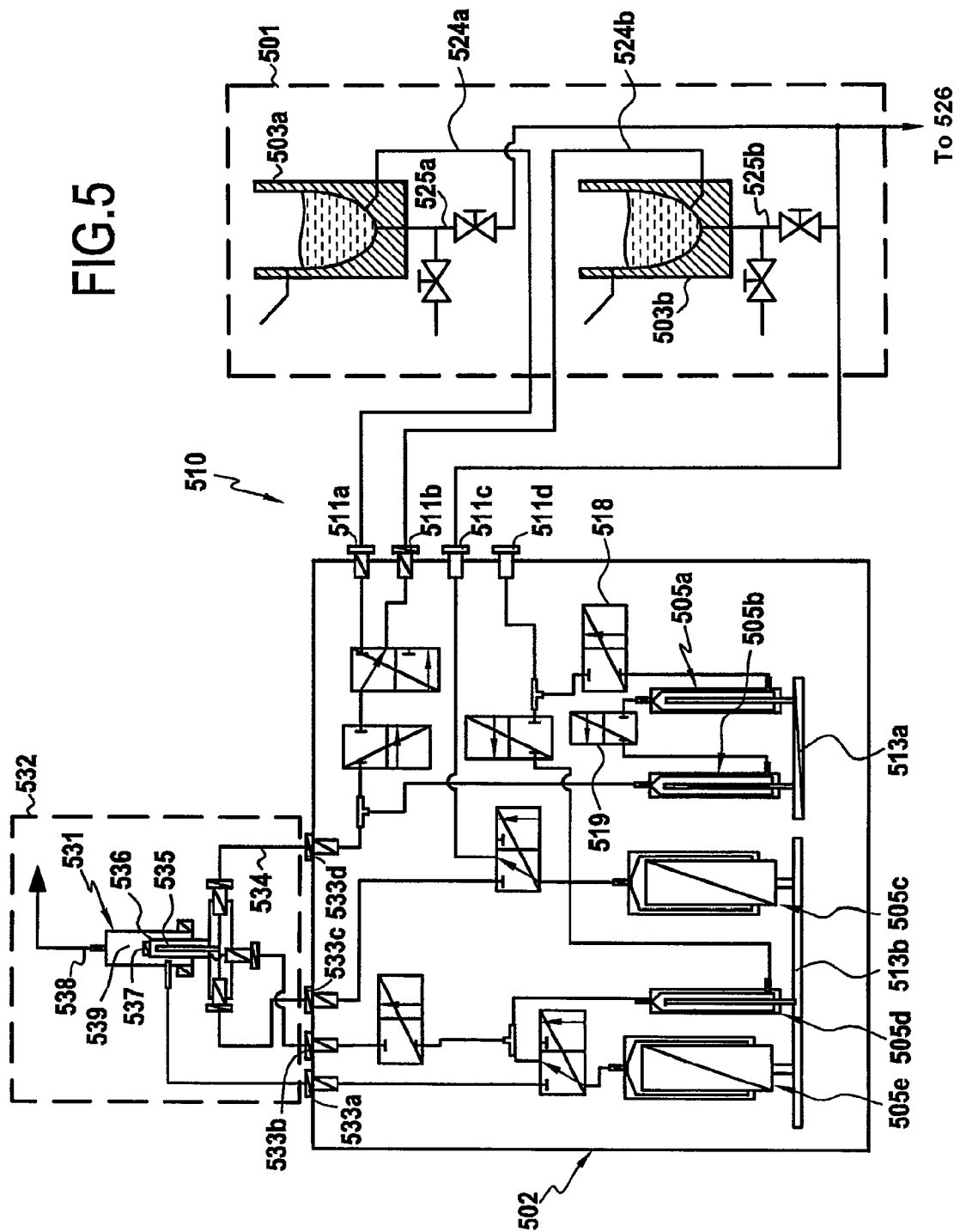

MODULAR DEVICE FOR ANALYZING A BIOLOGICAL FLUID, SUCH AS BLOOD

BACKGROUND OF THE INVENTION

The present invention relates to the general field of systems for analyzing a biological fluid such as blood, plasma, etc.

In particular, the invention applies to blood sample analyzers, also known as hematology analyzers.

The main hematological examination known as cell counting consists in counting the cellular elements contained in blood. The main elements are red cells, white cells, and platelets. This is an important diagnosis tool for doctors and vets.

Counting is usually performed in public or private medical analysis laboratories by qualified technicians. In some countries, doctors can also perform analyses in their offices. The number of counts performed daily is extremely variable and can lie in the range a few tests per day in a doctor's office to several thousands of tests in a very large laboratory, whether private or public.

The manufacturers of analysis systems are thus obliged to make available a wide range of different systems for satisfying the particular needs of their clients. Analysis systems are characterized by their rates of throughput, the number of hematological parameters they deliver, and the extent to which they are automated.

Depending on the level of a system within a range, the rate of throughput lies in the range 60 to 120 tests per hour, with the operator having a greater or smaller number of operations to perform manually and with the parameters delivered being more or less numerous: possibly being limited to counting cells, or else extended in particular to distinguishing subfamilies of white cells.

Manifold type hydraulic circuits have been known for a long time. The use of such circuits makes it possible to diminish considerably the number of pipes needed for connecting together the hydraulic components. This reduction makes it possible to increase the reliability of the device and thus to reduce maintenance. It can also happen that the use of manifolds makes it possible to reduce the risk of leaks and to increase the ability of fluid circuits to withstand reagents.

In particular, it is known to make a biological fluid analysis system on an acrylic support that supports hydraulic components. With manifold technology, the support includes at least two plates having circuits etched therein that enable channels to be defined when the two plates are assembled together side by side. The hydraulic components then used are, in particular dilution vessels, diaphragm valves controlled by pressure/suction switching, syringes, sampling valves, diaphragm pumps, pneumatic valves for controlling integrated diaphragm valves, etc.

U.S. Pat. No. 5,788,927 describes one such system. The acrylic support described in that document serves to implement a well specified group of functions and is therefore specific to a particular system. The support is made using a relatively large number of plates assembled together side by side, and it incorporates not only channels but also dilution vessels, and diaphragm valves controlled by pressure/suction switching. The support also serves as a support for a sampling valve, for diaphragm pumps, for pneumatic valves for controlling the integrated diaphragm valves, and for a heater.

The system described in that document is very compact since numerous functions are integrated in a common acrylic support. In contrast, that system does not present any flexibility in fabrication. It is dedicated to implementing a group of functions comprising at least preparing, injecting, and analyzing the fluid, such a system not being modular, e.g. for the purpose of increasing the number of analyses that it performs in parallel. Increasing the number of analyses performed in parallel requires an entire new system to be designed and fabricated.

French patent FR 2 862 387 in the name of C2 Diagnostics also describes such a systems in the form of a block of syringes with a plastics material support for preparing, injecting, and measuring out a fluid for analysis. The syringe block is independent and operates with an air pump. Solenoid valves are also integrated in the support, which support can be connected to an optical bench by means of hydraulic circuits carried by the support.

Nevertheless, the syringe block does not provide flexibility in fabrication. As in the device proposed in U.S. Pat. No. 5,788,927, the device incorporates a predetermined plurality of functions that is not variable within a given block. To add or modify functions, it is necessary to design a new syringe block.

Thus, for a given manufacturer, since the measurement technologies and the way in which mixtures of blood and reagents are prepared are often different depending on the level of a system within a range, each system in a range made in accordance with the teaching of the prior art is thus specific, and built using its own parts and requiring maintenance that is specific thereto.

OBJECT AND SUMMARY OF THE INVENTION

A main object of the present invention is to mitigate such drawbacks by proposing a modular device for implementation in a biological fluid analysis system, said modular device comprising functional modules, each comprising a support for supporting hydraulic components, the support including at least two plates having etched therein circuits that enable channels to be defined when the two plates are assembled side by side, which modular device is such that said functional modules comprise at least a preparation first functional module for preparing a fluid for analysis and supporting at least one dilution vessel, and an injection second functional module for injecting the fluid prepared in said dilution vessel towards an analysis unit, said first and second modules being connected to one another.

The term "preparation" is used herein to mean preparing a sample of fluid for analysis, and in particular the steps of diluting it with a diluent, mixing it with one or more reagents, and adding antibodies, enzyme(s), or indeed dye or dyes. Those steps are performed traditionally with the help of at least one dilution vessel, also referred to as a mixing vessel. The term "injection" is used to mean the steps of taking fluid from a dilution vessel and injecting it into an analysis unit in order to analyze the fluid.

With a modular device of the invention, biological fluid for analysis is prepared and injected using different functional modules. Functions that are common to a range of systems can thus be implemented in a given functional module in a manner that is independent from other functions that may differ as a function of level within the range.

Thus, only one kind of functional module is fabricated for each function that is common to an entire range. For example, fluid injection can be one of those functions. The manufacturer thus reduces the complexity and the number of different functional modules that need to be fabricated.

It is thus possible to retain fluid preparation characteristics while changing the way the fluid is injected and vice versa. The two main functions of an analyzer can thus be modular since they are performed using two distinct functional modules. This makes it possible to have a choice of characteristics for an analysis system depending on final requirements without it being necessary to change the entire system as happens at present.

Implementing different functions independently and separately also makes maintenance of the analysis system easy.

In an advantageous embodiment, the support for the injection functional module is fastened in substantially perpendicular manner to the support for the preparation functional module via one of the edge faces of the periphery of the two plates assembled side by side of the injection functional module.

This makes it possible to make the modular device and thus the analysis system more compact, while also making it easier for the system to be modular, e.g. making it easy to place a plurality of injection functional modules in parallel on the preparation module without increasing the overall rectangular bulk of the system. It then becomes possible to increase the rate of throughput of the analysis system without increasing its overall size. Furthermore, since such a disposition makes it possible to have short travel paths for the fluids, the volumes of fluid samples and of reagents that are required are thus reduced.

In an advantageous embodiment, the preparation and injection functional modules are connected together without using a pipe.

The term "pipe" is used herein to mean a tubular element, usually made of plastics material, that extends outside the functional modules and that is thus distinct from the channels present in the supports of said functional modules.

By eliminating pipes for making connections between functional modules, the risks of breakdowns are reduced and fabrication, setup, and maintenance of the device are simplified.

It is thus advantageous for at least one orifice passing through one of the support plates of the preparation functional module to be provided for connecting the injection functional module in a manner that is substantially perpendicular to said plate.

This makes it possible to shorten the path between the injection functional module and the preparation functional module connected together in perpendicular manner.

Advantageously, at least one orifice is provided in the edge face of the periphery of the injection functional module for connection to the through orifice of the preparation functional module.

A simple and easy connection without a pipe can then be provided by fitting the orifice passing through the preparation functional module to the orifice in the edge face of the injection module.

In an advantageous embodiment, at least one functional module is such that the hydraulic components are fastened to the outside of said support.

By way of example, the hydraulic components are selected from the following components: valves; syringes; and dilution vessels.

The term "fastened" is used herein to designate a direct and releasable mechanical connection between the supports of two functional modules or between a hydraulic component and the support of a functional module. By fastening the hydraulic components to the outside of the support, it continues to be possible to vary the number and the characteristics thereof, and the use of additional pipes is avoided.

In the state of the art, the various hydraulic components and the means for taking samples and fractioning blood that are not directly integrated in the plates are connected to one another by flexible pipes that become extremely numerous in a top-of-range apparatus. Such pipes need to be laid meticulously by operators during production. They tend to degrade over time, and they also require a large amount of expensive maintenance. Furthermore, they constitute a major source of incidents and thus of risk for the quality of analyses.

Furthermore, a survey of the hydraulic-component requirements for making a complete range of analysis systems shows that said requirements are limited and amount to little more than a few syringes of different volumes, to dilution vessels, to a specific dilution vessel that also makes it possible to perform photometric measurements of hemoglobin, and to at least one optical and/or impedance measurement vessel.

Advantageously in accordance with the invention, the hydraulic components are fastened to the outside of the functional modules and they are preferably used without pipes, thus making it possible to standardize them in the form of units. For example, the same model of syringe can be used in a plurality of systems.

Thus, the acrylic supports preferably do not incorporate components such as valves, syringes, or dilution chambers for the purpose of enabling a predetermined and precise group of functions to be provided as happens in the prior art. This means that the invention provides a system that is more modular.

Since the hydraulic components can then be made in large quantities, they are advantageously molded. Nevertheless they could also be machined.

It is also advantageous for the hydraulic components that are made to have fasteners and connection interfaces that enable them to be made interchangeable.

By means of the invention, the number of hydraulic components fastened on the preparation functional module can thus be varied as a function of the level of the system within the range.

In an embodiment, the modular device of the invention includes at least one preparation functional module comprising a plurality of connection interfaces for direct and parallel connection of a plurality of functional modules, each possessing a connection interface complementary to the connection interfaces of the preparation functional module, each connection interface being connected to at least one array of channels inside the preparation functional module.

Thus, in a preferred embodiment, the acrylic supports as used in the invention are used as rigid supports for hydraulic components and a plurality of functional modules with the purpose of connecting them together by channels. Since the supports forming the modules are rigid, they act as mechanical supports. This is a non-negligible advantage, since they avoid the use of structures dedicated to supporting the various components of the analysis system as happens at present.

By enabling the number of injection functional modules that are connected to a preparation functional module to be increased, the invention also makes it possible to fabricate analysis systems at different levels within a range by multiplying the rate of analysis throughput, and this is made possible using the same basic functional modules.

For this purpose, the connection interfaces are advantageously identical, while enabling a variety of functional modules to be connected, but they may equally well present characteristics that are distinct and adapted to the particular features of each type of functional module.

In a preferred embodiment, the preparation functional module includes one fluid inlet orifice per reagent that is to be introduced into a dilution vessel, and one waste outlet orifice, the waste outlet orifice being a single orifice for said modular device.

Thus, the functional modules connected to the preparation module are advantageously connected in such a manner that waste is centralized in the preparation module and evacuated via a single outlet orifice for the modular device. The term "waste" is defined as designating residues from cleaning vessels, residual dilutions or mixtures, dilutions or mixtures injected into measurement means, and dilutions or mixtures present in the channels.

The invention also provides a preparation functional module usable in a modular device of the invention and comprising a support for supporting hydraulic components, said support including at least two plates having circuits etched therein, enabling channels to be defined when the two plates are assembled together side by side, said preparation functional module supporting at least one dilution vessel and being suitable for being connected to a so-called injection second functional module for injecting the fluid prepared in said dilution vessel towards an analysis unit.

Advantageously, such a preparation module includes a plurality of connection interfaces for direct and parallel connection of a plurality of functional modules including at least one injection functional module, each module possessing a connection interface complementary to the connection interfaces of said preparation functional module, each connection interface being connected to at least one array of channels inside said preparation functional module.

In a preferred embodiment, the preparation functional module includes one fluid inlet orifice per reagent that is to be introduced into a dilution vessel, and one waste outlet orifice, said waste outlet orifice being a single orifice for said modular device.

The invention also provides an injection module suitable for use in a modular device of the invention and comprising a support for supporting hydraulic components, said support including at least two plates having circuits etched therein that enable channels to be defined when the two plates are assembled together side by side, said injection functional module being suitable for being connected to a so-called preparation functional module supporting at least one dilution vessel in order to inject the fluid prepared in said dilution vessel towards an analysis unit.

Finally, the invention provides a method of making a biological fluid analysis system, the method including a step of constructing a modular device, in which step at least a first preparation functional module for preparing the fluid to be analyzed is connected to a second injection functional module for injecting the prepared fluid towards an analysis unit, said functional modules each comprising a support for supporting hydraulic components, said support including at least two plates in which circuits are etched that enable channels to be defined when the two plates are assembled together side by side.

Finally, the invention provides the use of at least one functional module as described above in the fabrication of a biological fluid analysis system.

BRIEF DESCRIPTION OF THE DRAWINGS

Other characteristics and advantages of the present invention appear from the following description with reference to the accompanying drawings that show embodiments having no limiting character. In the figures:

FIG. 5 is a hydraulic circuit diagram of an injection functional module of the invention.

DETAILED DESCRIPTION OF AN EMBODIMENT

In the description below, elements that are similar from one figure to another are designated by references that are common, comprising two digits preceded by a digit that represents the number of the figure.

Figure 1:
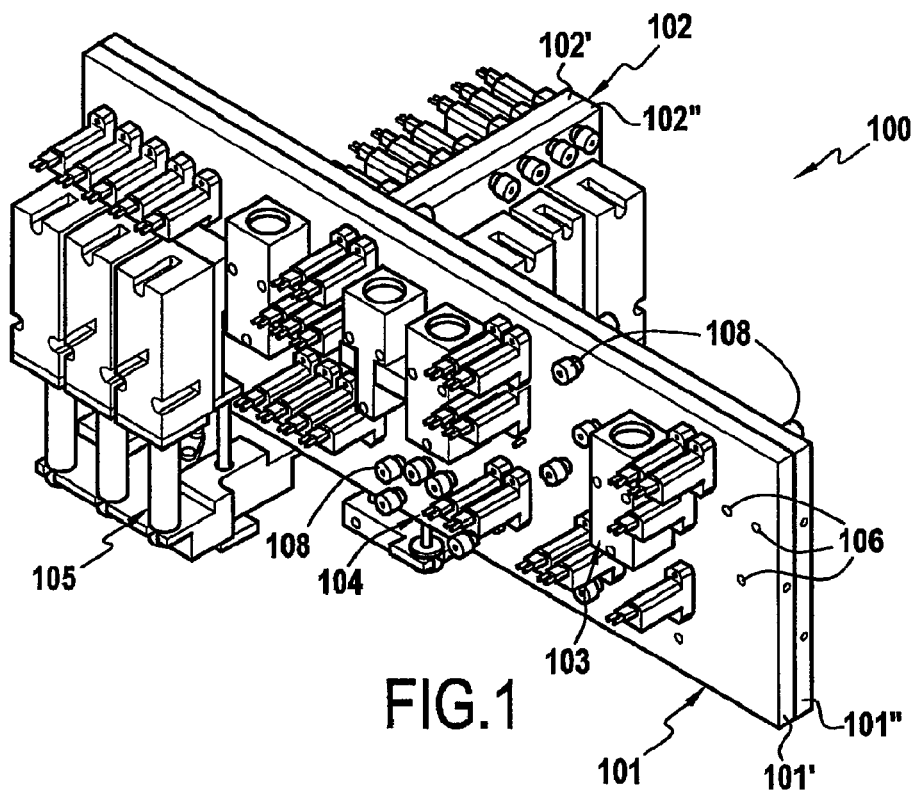
FIG. 1 is a perspective view of a modular device of the invention in a first application.

FIG. 1 is a perspective view of a modular device 100 of the invention.

As shown in FIG. 1, a modular device of the invention has at least one preparation functional module 101 on which there may be connected one or more standard functional modules, including at least one injection functional module 102.

Each of the functional modules includes at least two support-forming plates respectively referenced 101', 101" and 102', 102". Circuits are etched on the inside faces of each of the two pairs of plates. These circuits are symmetrical so that when the plates are assembled together side by side in pairs, as shown in FIG. 1, they define channels within the support formed by the plates, these channels enabling hydraulic components to be interconnected.

As can be clearly seen in this figure, the principle of the invention consists in implementing the main functions of an analysis system, namely preparing and injecting the fluid for analysis, on functional modules 101 and 102 that are distinct. As explained below, this ensures that the device is of a modular nature since it is possible to design an entire range of systems of different capacities and complexities using a limited number of parts.

In order to be able to perform the function to which it is dedicated, each functional module presents various hydraulic components fastened on the outside faces of the plates.

For this purpose, the preparation functional module 101 has the means required for performing dilutions, and these are provided as a function of the level within the range at which the modular device is to operate.

The hydraulic components needed for preparing dilutions comprise at least a dilution vessel 103, a valve 104, and a syringe 105, which elements are needed in particular for metering reagents. These hydraulic components are fastened to the outside of the support of the module 101. In known manner, a stepper motor actuating the syringes 105 enables speeds and volumes to be caused to vary while maintaining good accuracy.

The preparation functional module 101 is provided with connection interfaces 106 for connecting the hydraulic components. The term "connection interface" is used herein to mean an interface, generally constituted by orifices, that enables two functional modules or a functional module and a hydraulic component to be connected together without a pipe. A connection interface 106 advantageously comprises at least one fluid inlet orifice and at least one fluid outlet orifice. These orifices are advantageously through holes formed in one of the support plates of the functional module.

The channels etched in the plates constituting the preparation functional module 101 enable the connection interfaces, and thus more particularly the various hydraulic components, to be connected to one another.

The ability to fasten hydraulic components to the outside of the functional module makes it easy to modulate their functional capacities. In particular, on the preparation functional module, it is possible to add or remove a dilution vessel 103 in order to increase or decrease the number of dilutions that can be performed with this particular preparation module 101.

Connection interfaces that are not visible in FIG. 1 since they are disposed on the face to which the injection functional module is connected, are themselves dedicated to making connections with functional modules, and in particular with an injection functional module 102. By way of example, such connection interfaces are complementary to those shown in FIG. 6 for an injection module. Their shape is advantageously identical to the shape of the interfaces shown in FIG. 6, except that they are made perpendicularly to the faces of the preparation functional module.

The preparation functional module 101 is provided with connectors 108 capable of serving to connect the preparation functional module with the help of pipes to a functional module or to a hydraulic component.

In a simple embodiment of the invention, it is thus possible to envisage connecting the preparation functional module 101 with the injection functional module 102 with the help of pipes and such connectors 108.

The size of the preparation functional module 101 associated with a greater or smaller number of hydraulic components and functional modules that are connected thereto determines the size of the analysis system, its throughput rate, possibly its automation, and thus its level within a given range of systems.

The number of dilutions possible is closely tied to the positioning of the system in the range. A bottom-of-range device can often make do with a single dilution performed with one diluent, whereas a top-of-range system giving a greater number of hematological parameters and capable of operating more quickly requires a plurality of dilutions, that are performed with specific reagents, and that are generally about four in number.

In a range, the number of dilutions can vary significantly, and it is not always necessary for the blood to be fractioned. The principle of the invention makes it possible to leave the means for taking and fractioning the blood outside the preparation functional module, either in the form of hydraulic components fastened on the outside faces of the plates, or in the form of specific functional modules that are likewise fastened on the outside faces of the plate. For example, it is possible to envisage using a sampling valve as a hydraulic component fastened on the preparation functional module or as a functional module comprising a support manifold supporting the sampling valve, the support manifold being designed to be fastened on the preparation functional module.

This aspect whereby functions are made external in the form of hydraulic component(s) or of functional module(s) is particularly advantageously since it enables an analysis system to be customized as a function in particular of the desired throughput rate, the desired level of automation, and the parameters to be analyzed.

A preparation functional module equipped in accordance with the invention possesses functions that are well defined and separate from those of the functional modules to which it is connected. The invention makes it possible then to connect together varying numbers of functional modules in order to build up a system of a particular level in a range of systems. This is shown in FIGS. 1 and 2.

Figure 2:
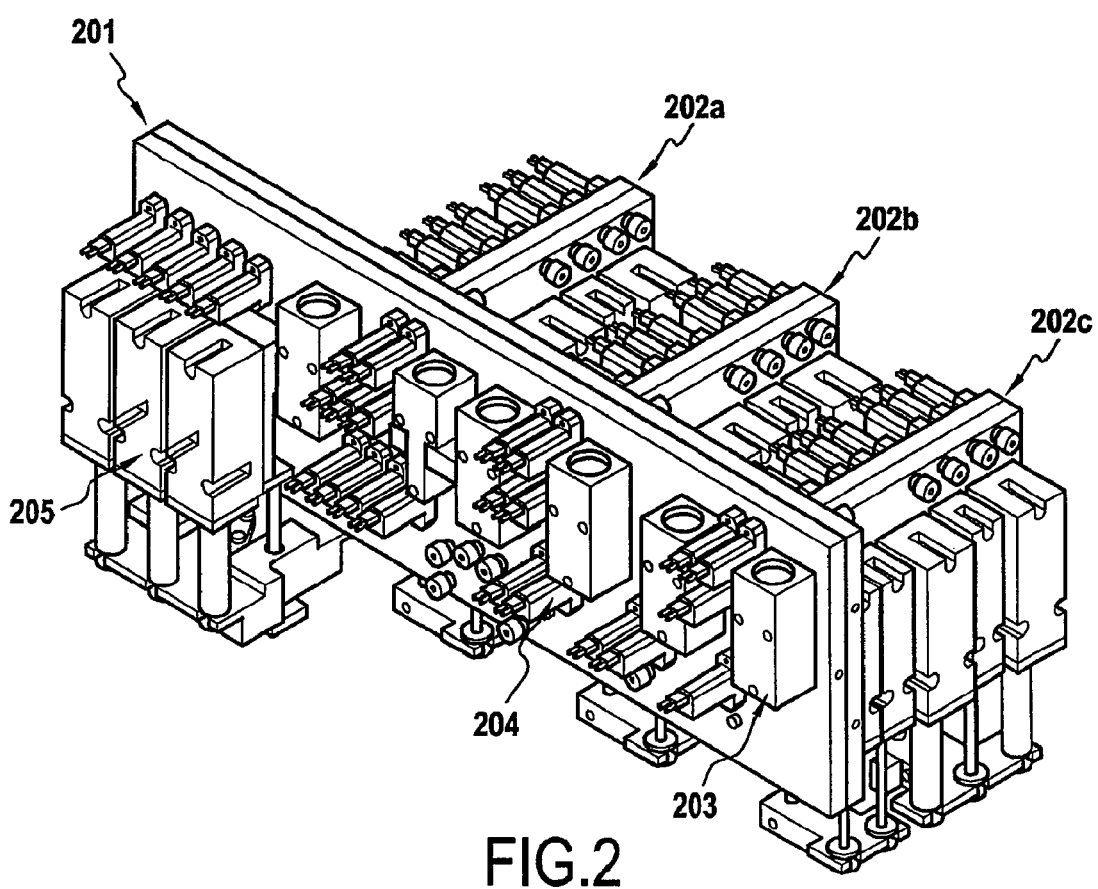
FIG. 2 is a perspective view of a modular device of the invention in a second application.

FIGS. 1 and 2 show clearly the modular nature of a modular device of the invention. These two figures show the same preparation functional module 101 that can be equipped to a greater or lesser extent, in particular by replacing the syringes and/or the valves by "straps" and by using syringes of different diameters that are mutually compatible and by connecting a varying number of functional modules thereto, in this case injection modules 102.

FIG. 1 shows a bottom-of-range device. The preparation functional module 101 is equipped with four dilution vessels 103, with valves 104, and with syringes 105. However this module could have only one dilution vessel and a small number of valves and syringes.

The preparation functional module 101 is equipped with a single injection functional module 102. Measurements are performed sequentially starting from one or more dilutions. Typically, a measurement relating to red cells is followed by one or two measurements relating to white cells.

Such a modular device is adapted to bottom-of-range systems for laboratories that do not require a high analysis throughput rate. It is also possible to produce a specific preparation functional module that is more compact, having only the portion needed for connection to a single injection functional module.

FIG. 2 shows a modular device for use in a top-of-range analysis system. The preparation functional module 201 is fitted with the same hydraulic component as the preparation functional module in FIG. 1, but in greater numbers. It is also fitted with three injection functional modules 202a, 202b, and 202c connected in parallel and enabling three series of measurements to be performed simultaneously from the dilutions carried out in the six dilution vessels 203. Such a modular device 200 is adapted to systems having high analysis throughput rates.

With this modular device 200, a plurality of dilutions can be performed simultaneously. Under such circumstances, at least the total quantity of blood required for all of the analyses is sucked in and then fractioned into a plurality of portions referred to as "aliquots", which are subsequently mixed in different dilution vessels with the appropriate reagents. This fractioning step is described in detail below and it is preferably performed outside the preparation functional module.

The invention is not restricted to the two configurations shown in FIGS. 1 and 2, it being possible to increase the number of functional module connection interfaces, it being possible to connect and fasten to the preparation functional module one or more functional modules or fractioning, measurement, etc. hydraulic components. It should also be observed that the preparation functional module may be a single module with a greater or lesser amount of equipment or presenting specific characteristics for each level in the range, for example being more compact, while the injection module remains the same. That does not remove the modular nature of analysis systems made using a modular device of the invention. A plurality of preparation modules adapted to each level of the range can thus advantageously be envisaged.

On the topic of the equipment for a preparation module, in the example shown in FIGS. 1 and 2, the number of vessels can vary over the range one to six vessels. The number of vessels chosen is a function of the so-called "incubation" times needed for performing the intended analyses, the desired rate of throughput, the number of parameters to be analyzed, Incubation time is typically ten to fifteen seconds and, in a device of the invention, it can thus be necessary to organize time shifts in the analysis cycle in order to take account thereof. Thus, certain vessels might no longer be suitable for use after a certain length of time has elapsed, while others continue to be used.

The advantage of having a plurality of vessels is the ability to optimize the use of vessels, in particular as a function of these incubation times. Two dilution vessels make it possible to perform the same analyses as four vessels, but sequentially, and therefore more slowly.

The use of dilution vessels is generally implemented with the help of software controlling the operation of the analysis system. When vessels are used efficiently, the rate of throughput can be increased significantly.

By way of example, the parameters analyzed are not only counting red cells, but also counting monocytes, lymphocytes, and granulocytes. Under such circumstances, a single vessel suffices. When extra analyses are included amongst the granulocytes concerning the quantities of neutrophils, basophils, and esophonils, it is necessary to use at least two vessels.

In the modular devices of FIGS. 1 and 2, the fact of bringing all of the vessels together on a preparation functional module and of connecting thereto at least one functional module for injection to an analysis unit makes it possible to have all of the dilution vessels of the analysis means close together. Generally, in the prior art, dilution vessels are implemented so as to be close to the analysis means and they are consequently far apart from one another. The quantity of waste produced in the connection pipes during analysis and the volumes of reagents and taken samples needed are then large.

In the invention, since the vessels are close to the measurement means and since, in general, an analysis system obtained with a modular device of the invention is compact, the quantity of waste is reduced as are the volumes of reagents and taken samples that are needed. This satisfies well requirements to save on reagents, to limit the sizes of samples taken, and to reduce waste, as are encountered in the field of analyzing biological fluids.

Analyzing a fluid, e.g. blood, is a method performed in several steps that are performed sequentially and independently with the help successively of the preparation functional module, the injection functional module, and other functional modules that are connected thereto. The combined operation of the various functional modules is described in detail below.

The first step of the analysis consists in mixing a fraction of the blood contained in the patient tube with a reagent. This operation, referred to as "dilution", is necessary at least to adapt the concentration of cells to the analysis unit and to prepare them specifically as a function of the measurement to be made thereafter. It is also used to destroy a specific family of cells, e.g. red cells, so as to leave only white cells, thus making it easier to count them or to distinguish them in subfamilies or indeed to color the nuclei of the cells or to mark them with specific antibodies.

A first known fractioning method consists in using a sampling valve. The blood is sucked through the sampling valve and fills loops of predetermined volume. The sampling valve is then switched so as to push the blood contained in each loop into different dilution vessels containing corresponding reagents.

A second fractioning method, described in French patent FR 2 770 299, consists in pushing the fractions of blood contained in a needle into a stream of reagent over each dilution vessel.

In those two methods, the mixing performed in the dilution vessels needs to be very accurate. The metering element in the most widespread use for reagent is the syringe and its volume is adapted to the quantity to be measured out.

As mentioned above, the preparation functional module supports the hydraulic components, syringes, valves, vessels, and hydraulic connection circuits for performing the dilution(s) after fractioning.

Often, it is necessary to comply with a so-called incubation time to ensure that the reaction between the blood and the reagent can take place completely and also to ensure an accurate reaction temperature. By means of the invention, this step is performed in the preparation functional module independently of the other steps.

Figure 3:
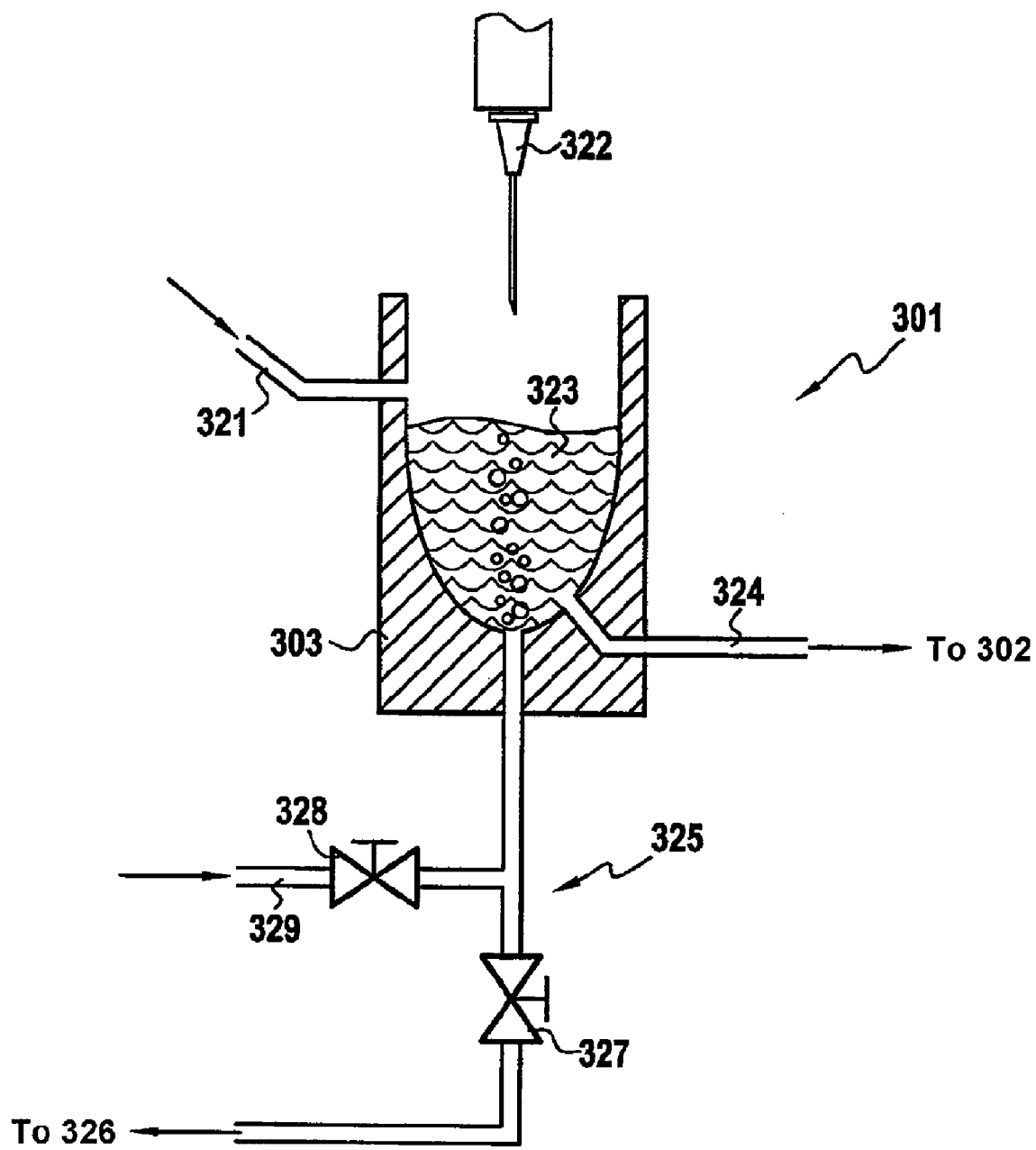
FIG. 3 is a diagrammatic illustration of the operation of a preparation functional module of the invention.

FIG. 3 shows the operation of a preparation functional module 301 of the invention. The preparation functional module 301 includes a dilution vessel 303. A sample that has been taken arrives either under thrust from a reagent via a channel 321 of the preparation functional module 301, or via a sample-taking needle 322, depending on the fractioning method that has been selected. The reagent arrives via the channel 321 either after the sample for analysis which it pushes into the dilution vessel, or else alone, likewise depending on the fractioning method that has been selected.

In order to ensure good mixing of the reagent with the fluid for analysis, the dilution vessel is advantageously provided with means for sending air into the mixture obtained in the dilution vessel via a channel 329 and a valve 328.

The dilution or mixture 323 that is obtained is optionally left to stand for a certain incubation time in the vessel in order to comply with reaction kinetics.

In order to make injection possible, the dilution vessel 303 is connected to a channel 324 leading to an injection functional module 302 that is connected to the preparation functional module 301. The mixture 323 is taken by the injection functional module 302 via said channel 324 in the manner described in detail below.

The remainder of the mixture that is not taken is extracted and evacuated by a channel 325 connected through a valve 327 to a waste outlet orifice 326 that is advantageously a single orifice for the modular device in which the preparation functional module 301 is implemented.

After the dilution step, the following step is injecting the fluid for analysis into an analysis unit, where "analysis" is a general term that includes counting cells.

An analysis unit is preferably a measurement functional module made in application of the principles of the invention, but it could also be a measurement device connected to the modular device of the invention by means of pipes.

Main known measurement methods use impedance variation or optical means.

The method of measuring by impedance variation, known as the Coulter method after the name of its inventor and described in U.S. Pat. No. 3,259,842 granted on Jul. 5, 1966, consists in mixing the cells in a saline solution and then in sucking them through a calibrated orifice of small size, generally having a diameter lying in the range 50 micrometers ($\mu m$) to 100 $\mu m$, and in which an electric current flows. Each cell passing through the orifice behaves like an insulator and modifies the electric current, thereby generating a run of pulses proportional to the volume of the cells and capable of being counted and measured. That method can be implemented directly on a dilution vessel as fastened on the preparation functional module of the invention or in a measurement unit towards which a dilution is injected.

An important improvement of the method consists in centering the cells in the orifice with the help of a fluid also known as a sheathing fluid.

The sheathing method, well known to the person skilled in the art, serves to center the path of the cells as they pass through the measurement orifice. The effect of this improvement is to limit the effect of cells passing through in pairs due to the concentration of the mixture and the small size of the cells relative to the diameter of the measurement orifice. The quality of the electrical signal is improved and enables better processing to be performed subsequently by the electronics.

The method of centering cells in measurement means by a sheathing fluid, also known as hydraulic focusing of the cells, is essential when methods are performed by optical means alone, and constitutes an important improvement when measurements are performed by impedance. As a counterpart, it requires additional hydraulic means, and thus additional costs, and that generally constitutes a brake on its application in bottom-of-range systems.

With the invention, the additional cost can be compensated by producing a larger quantity associated with generalizing hydraulic focusing for all of the systems in a range. Such generalization also makes it possible to have a constant level of quality in the analyses regardless of the level of the system in the range.

The measurement technique using an optical method consists in causing cells that have previously been centered in an optical capillary tube by a sheathing fluid to flow past a light source that is focused on the cells. Counting and measurement can be performed by making use of the absorbence of a cell, its ability to diffract light at various angles, or its fluorescence after specific dying, or marking by antibodies.

Both methods can be combined. For example, French patent FR 2 653 885 describes a circulation vessel enabling both types of measurement to be combined.

Figure 4A:
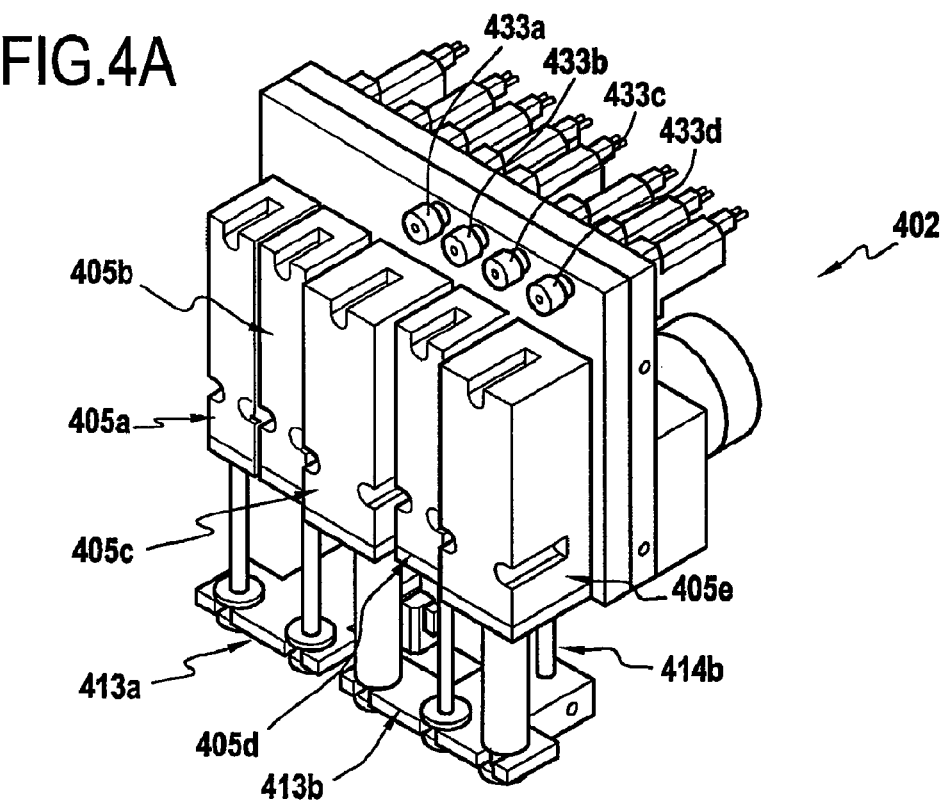
FIGS. 4A and 4B are two perspective views of an injection functional module of the invention.
Figure 4B:
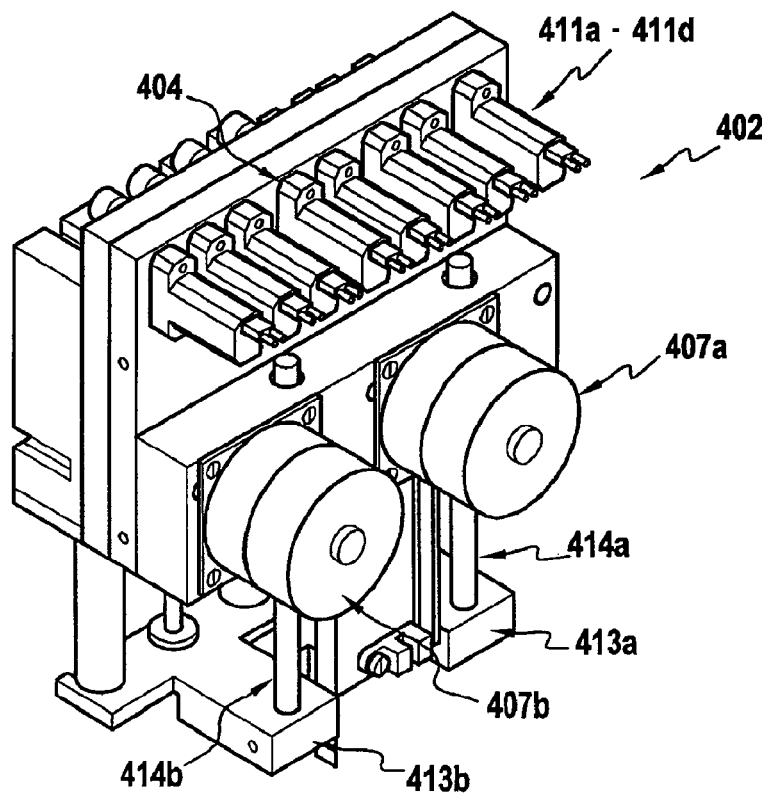

As shown in FIGS. 4A and 4B, the injection functional module 402 combines various hydraulic components fastened to the outside of the plates forming the injection functional module 402 in order to be capable of injecting the fluid for analysis from a dilution vessel of a preparation functional module connected via a connection interface 410 having orifices 411a, 411b, 411c, 411d placed on the edge face (not shown) of the injection functional module 402, towards a unit for performing analysis by counting cells and connected to connectors 433a, 433b, 433c, and 433d. Advantageously, these connectors are the orifices of a connection interface in the meaning of the invention. Five syringes 405a, 405b, 405c, 405d, and 405e, a plurality of valves 404, and two motors 407 are fastened on the injection functional module 402. These hydraulic components are amongst the hydraulic means necessary for injecting cells with hydraulic focusing towards a cell counter unit.

Motors 407a and 407b are connected to the syringes via brackets 413 and 413b in order to move them. The motors are of the stepper type, which makes it possible to obtain great accuracy in the volumes measured out and which make it easy to vary injection speeds for better adaptation to the cells for analysis. Racks 414a and 414b serve to transform the rotary motion of the motors 407a and 407b into linear motion. It should be observed that the invention is not restricted to this particular configuration.

The injection functional module 402 shown by way of example in FIG. 4 is particularly suitable for feeding fluid, and consequently cells, to an optical vessel of the kind described in French patent FR 2 653 885.

In accordance with the principles of the invention, the optical vessel is preferably implemented on an optical measurement functional module that is independent and that supports at least said measurement optical vessel and an optical bench.

In known manner, such a vessel makes it possible to associate an impedance measurement together with at least one optical measurement performed using absorbence, diffraction, or fluorescence. The optical measurements may be combined. The technique selected depends on the type of cell for analysis. In contrast, the hydraulic means used remain identical, and therefore, in accordance with the principles of the invention, they can be generalized in a standard injection functional module and regardless of the type of measurement that has been selected.

FIG. 5 is a hydraulic circuit diagram of an injection functional module 502 as shown in FIG. 4.

The injection functional module 502 is connected to an optical measurement vessel 531 via connectors 533a, 533b, 533c, 533d that preferably enable direct connections to be made without pipes to an optical measurement functional module 532 represented by dashed lines in FIG. 5 and constituting an analysis unit. It is possible to make such a measurement functional module that is connected directly to the module 502 of the invention when the measurement assembly is small in size.

The injection functional module 502 is also connected by connectors 511a, 511b to one or two dilution vessels 503a and 503b supported by a preparation module 501 shown diagrammatically in this figure.

Syringes 505a, 505b, 505c, 505d, and 505e fastened on the injection functional module 502 are split into two groups. Each group of syringes is actuated by a single motor, shown in FIG. 4 under the references 407a and 407b. The syringes 505a and 505b are mechanically coupled together by a bracket 513a, while the syringes 505c, 505d, 505e are coupled together by a bracket 513b.

The group of syringes 505a, 505b serves more particularly for injection purposes while the group 505c, 505d, and 505e is used more specifically for establishing the sheaths and for loading the sample from or one or two dilution vessels.

A measurement cycle begins by loading the sample for analysis in a measurement loop 534 from one or two dilution vessels of the preparation functional module 501 connected to the inputs 511a or 511b. A valve 516 serves to select the dilution vessel. Loading is performed by the syringe 505c which is pulled so as to suck in liquid from the dilution vessel(s) in the loop 534.

The sample for analysis is then pushed by the syringe 505b or by the syringes 505a and 505b into an injector 535 depending on the state of the valves 518 and 519. This disposition makes it possible to select the volume range for injection by associating the volume of both syringes 505a and 505b when the volume is high.

The syringe 505d serves to create the sheath around the cells in a chamber 536 in order to center them while passing through an impedance counting orifice 537.

The syringe 505e serves to create a second sheath in a measurement chamber 539 within which the cells pass in front of optical measurement means (not shown) before leaving via an orifice 538, from which waste is evacuated.

The waste is then preferably directed either to the injection functional module 502 via a pipe or via a channel before being directed to the preparation functional module 501 that centralizes and collects waste, or else directly towards the preparation functional module 501, e.g. via a pipe and without passing through the injection functional module 502.

The inlet 511d enables the sheathing liquid to enter.

The outlet 511c enables the waste to be evacuated, in particular the waste present in the channels of the injection functional module, being pushed by the syringe 505c towards the preparation functional module 501.

It is possible to eliminate the valve 518 and the syringe 505a when the functional module 502 is to continue working in the same volume range in order to optimize the injection functional module. Under such circumstances, the components are replaced by a hydraulic strap. The manifold remains unchanged.

It is possible to eliminate the vessel 516 and the inlet 511b when the functional module is always to work from a single dilution. Under such circumstances, the components are placed by a hydraulic strap. The manifold remains identical.

The syringes are mechanically interchangeable and the volumes of the syringes 505a, 505b, and 505d are selected as a function of the application.

The injection functional module 502 is independent and can manage all of the hydraulic steps needed for creating measurement conditions suitable for counting the various families of cells from one or more dilutions prepared for this purpose. It can load cells for analysis from two different vessels and it can adapt the range of the volume for analysis by selecting one syringe or by combining the volumes of two syringes.

This point is important in order to be able to go from analyzing red cells which requires a sample of about 3 microliters ($\mu$L) to analyzing white cells which requires a sample of 100 $\mu$L to 200 $\mu$L.

Figure 6:
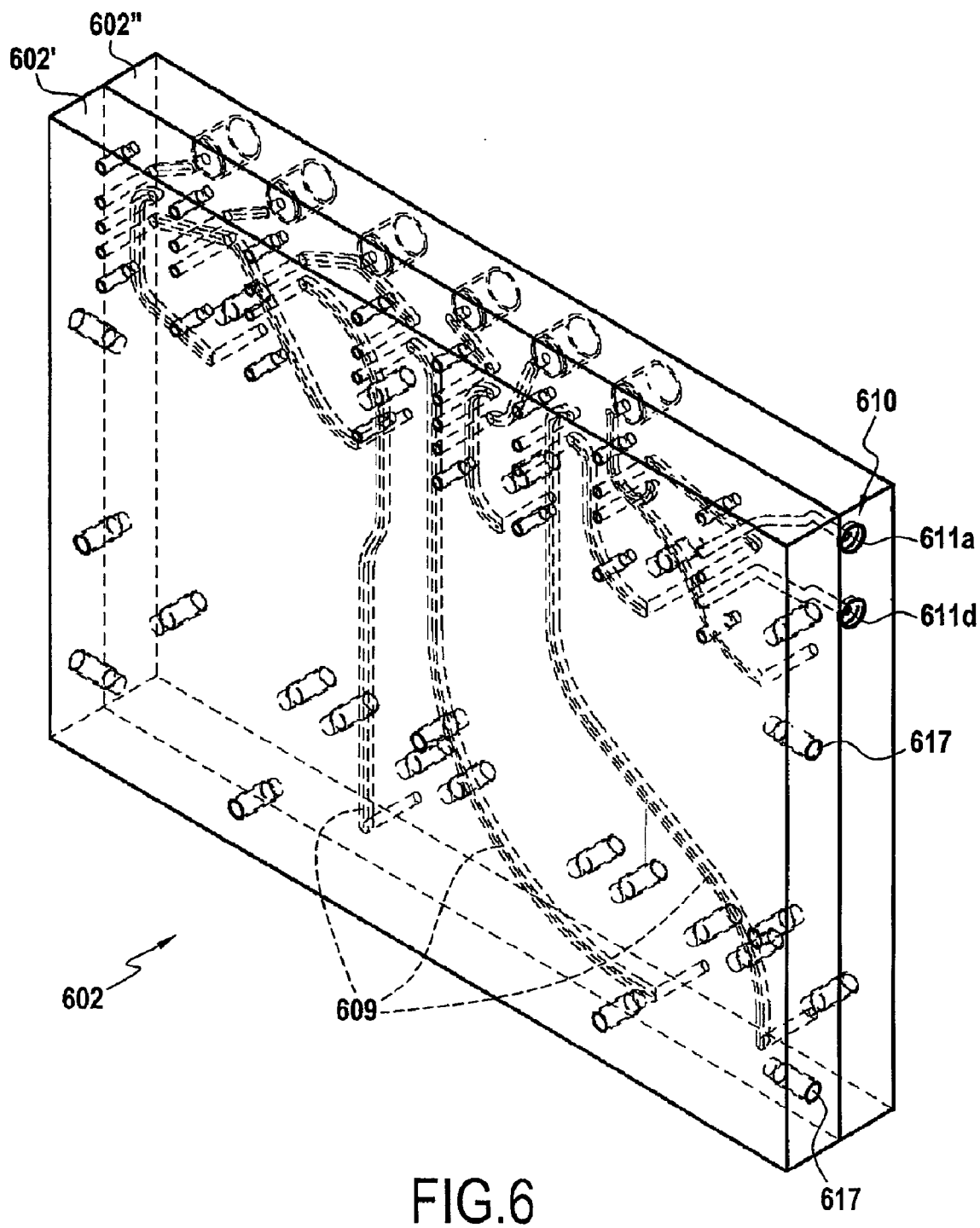
FIG. 6 shows a plate for assembling in an injection functional module of the invention.

FIG. 6 shows an example of the circuits 609 shown in dashed lines, that are etched in the plates 602' and 602" of the injection functional module 602 as shown in FIG. 4.

These circuits 609 open out via orifices that pass through one and/or the other of the plates. These orifices are dedicated to connecting hydraulic components or to connecting functional modules such as the preparation functional module.

The injection functional module 602 is advantageously provided with a connection interface 610 placed on an edge face of the outline defined around the two plates 602' and 602" when assembled together. This connection interface 610 has at least one fluid inlet orifice 611a connected by a hydraulic circuit to a valve, as shown in the hydraulic circuit diagram of FIG. 5, and at least one fluid outlet orifice 611d.

It should be observed that the orifices 611a and 611d can be centered or slightly off-center, as shown in FIG. 6, in the edge face of the injection module 602. This is the result of the way in which the channels of the manifold are made.

It will easily be understood that although the embodiment shown in FIG. 6 has only two orifices, other additional fluid inlet orifices, in particular those referenced 511b and 511c in FIG. 5, could also be implemented in similar manner in an injection functional module of the invention.

An O-ring (not shown) placed around the periphery of each orifice and of shape complementary thereto on a preparation functional module serves to seal the connection with the preparation module, in combination with means for holding two functional modules in position. Such holder means are constituted, for example, by screws passing through the preparation module and screwing into holes 617 provided for this purpose.

The ability to connect the injection functional module(s) 602 directly on the preparation functional module reduces the number of pipes and makes it possible to have channels that are as short as possible between both types of functional module.

Such a connection interface 610 serves to connect the injection functional module 602 directly via its edge face to the preparation functional module 601 without using a pipe.

The invention thus makes it possible to make up an analysis system around a modular device based on central use of a preparation functional module having functional modules connected thereto, including at least one injection module.

Based on the use of manifolds, the invention also makes it possible to solve a certain number of technical problems including steric hindrance and the difficulties of maintenance due to the use of pipes.

The preparation functional module presents properties similar to those of an electronics card having electronic components fastened thereto. Here the components are hydraulic components or functional modules. The preparation functional module acts as an "intelligent base" capable both of acting as a compact support of the entire analysis system and also of preparing samples for analysis. Hydraulic components and functional modules that are as standard as possible are connected thereto a manner that is simple and direct. The principle of the invention makes it possible to form various modular devices by associating a preparation functional module with at least one injection functional module, in order to produce a complete range of systems with very few different parts.

Each of the hydraulic components and functional modules connected to the preparation functional module is fastened thereto with the help of screws, snap-fasteners, or any other holder means not shown specifically in the figures and known to the person skilled in the art.

Since the principles of the invention make it possible to separate producing the various functions of an analysis process into as many independent functional modules that can be connected directly to one another in series or in parallel depending on the functions they implement, it is possible to develop one measurement functional module carrying an optical measurement bench that is dedicated rather to small devices and another functional module dedicated rather to large devices, one sample-taking and/or blood fractioning functional module dedicated rather to small devices and a second dedicated rather to large devices, etc.

In addition, developing standard functional modules makes it possible to fabricate systems having different levels within a range by arranging the various functional modules in different manners or in different numbers within a modular device of the invention.

On the principle of the invention, it is thus possible to develop functional modules for each of the functions provided by an analysis system. Such functional modules are constituted in particular by a functional module for preparing a sample and an injection functional module, but also by an optical measurement functional module, a functional module for taking samples and fractioning blood (sampling valves supported by modules), a functional module for biochemical analysis suitable in particular for being connected directly to the preparation functional module without passing via an injection functional module, an extraction functional module, a functional module for cleaning dilution vessels, a sample-taking functional module, etc.

The various functional modules are advantageously developed to be connected and operated directly, they are suitable for being connected to one another, and they are advantageously capable of being connected directly without needing adapters. It then becomes possible to produce a complete range of analysis systems that are also modular by using a smaller number of parts, typically about fifteen.

It is also possible to fabricate a system by placing a sample-taking device beside a modular device in which a plurality of injection functional modules are connected in parallel to a common preparation functional module as shown in FIG. 2, each of the injection modules being in turn connected in series with a measurement module.

It is emphasized that using such functional modules capable of being connected in series, e.g. a preparation functional module followed by an injection functional module followed by a measurement functional module, or in parallel, e.g. a plurality of injection functional modules connected in parallel with a preparation functional module, also enables fabrication and maintenance to be simplified and enables space to be saved. It is possible to obtain an analysis system that is easy to handle, modular, compact, and capable of performing analyses at high rates of throughput should that be necessary.

Finally, it should be observed that the characteristic whereby the modules can be fastened together in such a manner as to be substantially perpendicular to one another is a characteristic that is independent of the nature of the fastened-together functional modules and that is particularly advantageous from the point of view of the overall size of the analysis system.

Nevertheless, this does not mean that functional modules operating in series, e.g. a preparation functional module followed by an injection functional module cannot be fastened to one another in some other way, for example so as to be physically parallel being interconnected by short columns between one another. Although this is less advantageous, in particular from the maintenance point of view, such an embodiment is covered by the invention. It can turn out to provide greater compactness when hydraulic components supported by the functional modules are integrated in the support instead of being fastened on an outside face of the support.

Under all circumstances, the use of a preparation functional module centralizing the preparation of samples and on which one or more functional modules are connected makes it possible not only to obtain great compactness and to shorten fluid paths, thereby reducing the quantity of waste, but also avoids using other conventional support means such as metal structures carrying the various hydraulic components. The support of the preparation module formed by two rigid plates performs the mechanical support function in a manner that is advantageous and simple.

What is claimed is:

1. A modular device for implementing in a biological fluid analysis system, said modular device comprising functional modules each comprising a support for supporting hydraulic components, the support including at least two plates having etched therein circuits that enable channels to be defined when the two plates are assembled side by side, wherein said functional modules comprise at least a preparation first functional module for preparing a fluid for analysis and supporting at least one dilution vessel, and an injection second functional module for injecting the fluid prepared in said dilution vessel towards an analysis unit, said first and second modules being connected to one another, wherein the support for the injection functional module is fastened substantially perpendicular to the support for the preparation functional module via one of the edge faces of the periphery of the two plates assembled side by side of the injection functional module.

2. The modular device according to claim 1, in which the preparation and injection functional modules are connected together without using a pipe.

3. The modular device according to claim 1, in which at least one orifice passing through one of the support plates of the preparation functional module is provided for connecting the injection functional module in a manner that is substantially perpendicular to said plate.

4. The modular device according to claim 2, in which at least one orifice passing through one of the support plates of the preparation functional module is provided for connecting the injection functional module in a manner that is substantially perpendicular to said plate, and in which at least one orifice is provided in the edge face of the periphery of the injection functional module for connection to the through orifice of the preparation functional module.

5. The modular device according to claim 1, in which at least one functional module is such that the hydraulic components are fastened to the outside of said support.

6. The modular device according to claim 5, in which the hydraulic components are selected from the group consisting of valves; syringes; dilution vessels; and sampling valves.

7. The modular device according to claim 1, including at least one preparation functional module comprising a plurality of connection interfaces for parallel connection of a plurality of functional modules, each possessing a connection interface complementary to the connection interfaces of the preparation functional module, each connection interface being connected to at least one array of channels inside the preparation functional module.

8. The modular device according to claim 1, in which the preparation functional module includes one fluid inlet orifice per reagent that is to be introduced into a dilution vessel, and one waste outlet orifice, the waste outlet orifice being a single orifice for said modular device.

9. A preparation functional module for a modular device according to claim 1, comprising a support for supporting hydraulic components, said support including at least two plates having circuits etched therein, enabling channels to be defined when the two plates are assembled together side by side, said preparation functional module supporting at least one dilution vessel and being configured to be connected to the injection second functional module for injecting the fluid prepared in said dilution vessel towards an analysis unit.

10. The preparation functional module according to claim 9, including a plurality of connection interfaces for direct and parallel connection of a plurality of functional modules including at least one injection functional module, each module possessing a connection interface complementary to the connection interfaces of said preparation functional module, each connection interface being connected to at least one array of channels inside said preparation functional module.

11. The preparation functional module according to claim 9, including one fluid inlet orifice per reagent that is to be introduced into a dilution vessel, and a waste outlet orifice, said waste outlet orifice being a single orifice for said modular device.

12. A biological fluid analysis system including a modular device according to claim 1, the modular device comprising at least one preparation first functional module for preparing the fluid to be analyzed which first module is connected to an injection second functional module for injecting the prepared fluid towards an analysis unit, said functional modules each comprising a support for supporting hydraulic components, said support including at least two plates in which circuits are etched that enables channels to be defined when the two plates are assembled together side by side, wherein the support for the injection functional module is fastened substantially perpendicular to the support for the preparation functional module via one of the edge faces of the periphery of the two plates assembled side by side of the injection functional module.

13. A system for fabrication of a biological fluid analysis comprising at least one preparation functional module according to claim 9.

14. A system for fabrication of a biological fluid analysis comprising at least one preparation functional module according to claim 11.

15. A method of making a biological fluid analysis system, the method comprising constructing a modular device according to claim 1, wherein constructing comprises:

connecting at least one preparation first functional module for preparing the fluid to be analyzed to an injection second functional module for injecting the prepared fluid towards an analysis unit, said functional modules each comprising a support for supporting hydraulic components, said support including at least two plates in which circuits are etched that enables channels to be defined when the two plates are assembled together side by side, and fastening the support for the injection functional module substantially perpendicular to the support for the preparation functional module via one of the edge faces of the periphery of the two plates assembled side by side of the injection functional module.

* * * * *